(12) United States Patent
Crucs

(10) Patent No.: US 9,579,073 B2
(45) Date of Patent: Feb. 28, 2017

(54) SYSTEM AND METHOD FOR DENTITION SPECIFIC IMAGE ENHANCEMENT

(75) Inventor: Kevin M. Crucs, Copley, OH (US)

(73) Assignee: Apteryx, Inc., Akron, OH (US)

( * ) Notice: Subject to any disclaimer, the term of this patent is extended or adjusted under 35 U.S.C. 154(b) by 1988 days.

(21) Appl. No.: 12/775,681

(22) Filed: May 7, 2010

(65) Prior Publication Data

US 2011/0274332 A1 Nov. 10, 2011

(51) Int. Cl.
*A61B 6/14* (2006.01)
*A61B 6/00* (2006.01)

(52) U.S. Cl.
CPC .............. *A61B 6/14* (2013.01); *A61B 6/5294* (2013.01)

(58) Field of Classification Search
USPC .............. 382/128, 132; 378/38–40, 108, 195
See application file for complete search history.

(56) References Cited

U.S. PATENT DOCUMENTS

| | | | |
|---|---|---|---|
| 4,589,121 A | 5/1986 | Makino | |
| 4,882,494 A | 11/1989 | Rogers et al. | |
| 4,907,156 A | 3/1990 | Doi et al. | |
| 4,954,972 A | 9/1990 | Sullivan | |
| 5,093,852 A | 3/1992 | Nishikawa et al. | |
| 6,454,460 B1 | 9/2002 | Ramanathan et al. | |
| 6,471,399 B1 | 10/2002 | Zylka et al. | |
| 6,505,966 B1 | 1/2003 | Guru | |
| 6,630,938 B1 | 10/2003 | Nanni | |
| 7,006,600 B1 | 2/2006 | Krema et al. | |
| 7,027,160 B2 | 4/2006 | Sperling | |
| 7,189,000 B2 | 3/2007 | Miyauchi et al. | |
| 7,580,502 B2 * | 8/2009 | Dalpiaz et al. | 378/40 |
| 2002/0085664 A1 | 7/2002 | Bromberg et al. | |
| 2002/0085673 A1 * | 7/2002 | Rinaldi et al. | 378/108 |
| 2004/0073092 A1 | 4/2004 | Dale | |
| 2004/0109528 A1 | 6/2004 | Nukui et al. | |
| 2004/0196960 A1 | 10/2004 | Tanigawa et al. | |
| 2005/0067578 A1 | 3/2005 | Ueno et al. | |
| 2005/0084826 A1 | 4/2005 | Pilaro et al. | |
| 2006/0049358 A1 | 3/2006 | Oumi et al. | |
| 2006/0088140 A1 | 4/2006 | Fahrig et al. | |
| 2009/0297003 A1 | 12/2009 | Wong et al. | |
| 2009/0310741 A1 | 12/2009 | Borghese et al. | |

OTHER PUBLICATIONS

Peter Mah DMD, W. Doss McDavid Phd., "Digital Sensor Evaluation," University of Texas Health Science Center San Antonio, Nov. 29, 2007.

* cited by examiner

*Primary Examiner* — Joseph Burgess
(74) *Attorney, Agent, or Firm* — Hahn Loeser & Parks LLP

(57) ABSTRACT

Systems, methods, and computer readable media to automatically tailor image parameter settings used in a dental X-ray imaging system. At least one dentition characteristic and at least one non-dentition characteristic are selected and used to automatically determine at least one X-ray exposure setting for a patient to be imaged. The at least one dentition characteristic, the at least one non-dentition characteristic, and the at least one X-ray exposure setting are used to automatically generate a set of image parameter settings capable of being applied to acquired X-ray image data, being representative of the dentition of the patient.

43 Claims, 8 Drawing Sheets

FIG. 2

Example Dentition Characteristics

- Tooth identifier
- Capped tooth flag
- Tooth filling flag
- Teeth bridge work flag
- Tooth implant flag
- Root canal flag
- Cracked/broken tooth flag
- Strong/weak enamel flag
- Braces flag
- Image type

Example Non-dentition Characteristics

- Gender
- Race (Ethnicity)
- Weight
- Height
- Age
- Pregnancy status
- Species

Example X-ray Exposure Settings

- Exposure time setting
- Current setting
- KVP setting
- mAs setting

Example Image Parameter Settings

- Brightness setting
- Contrast setting
- Gamma setting
- Filter setting
- Threshold setting
- Color map

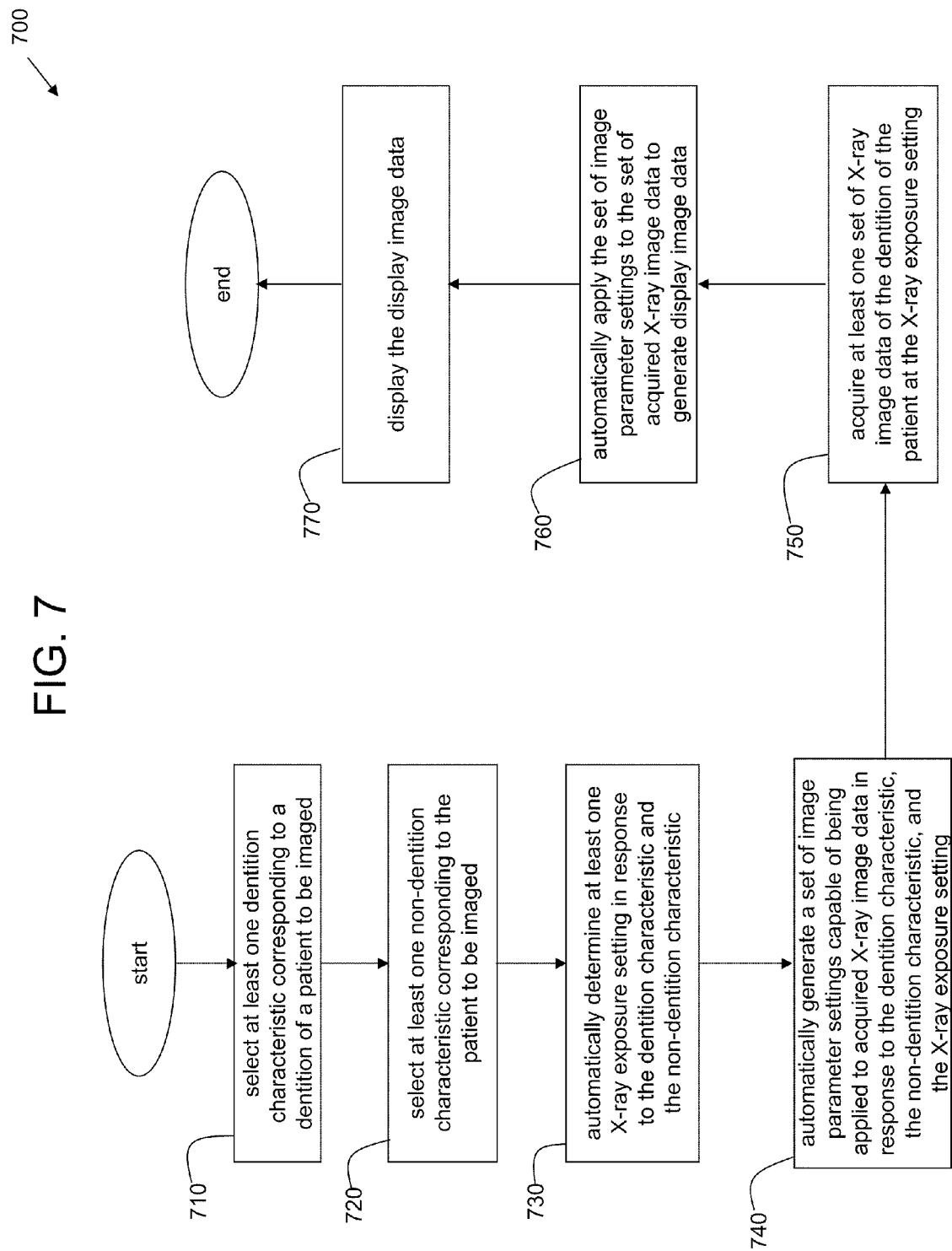

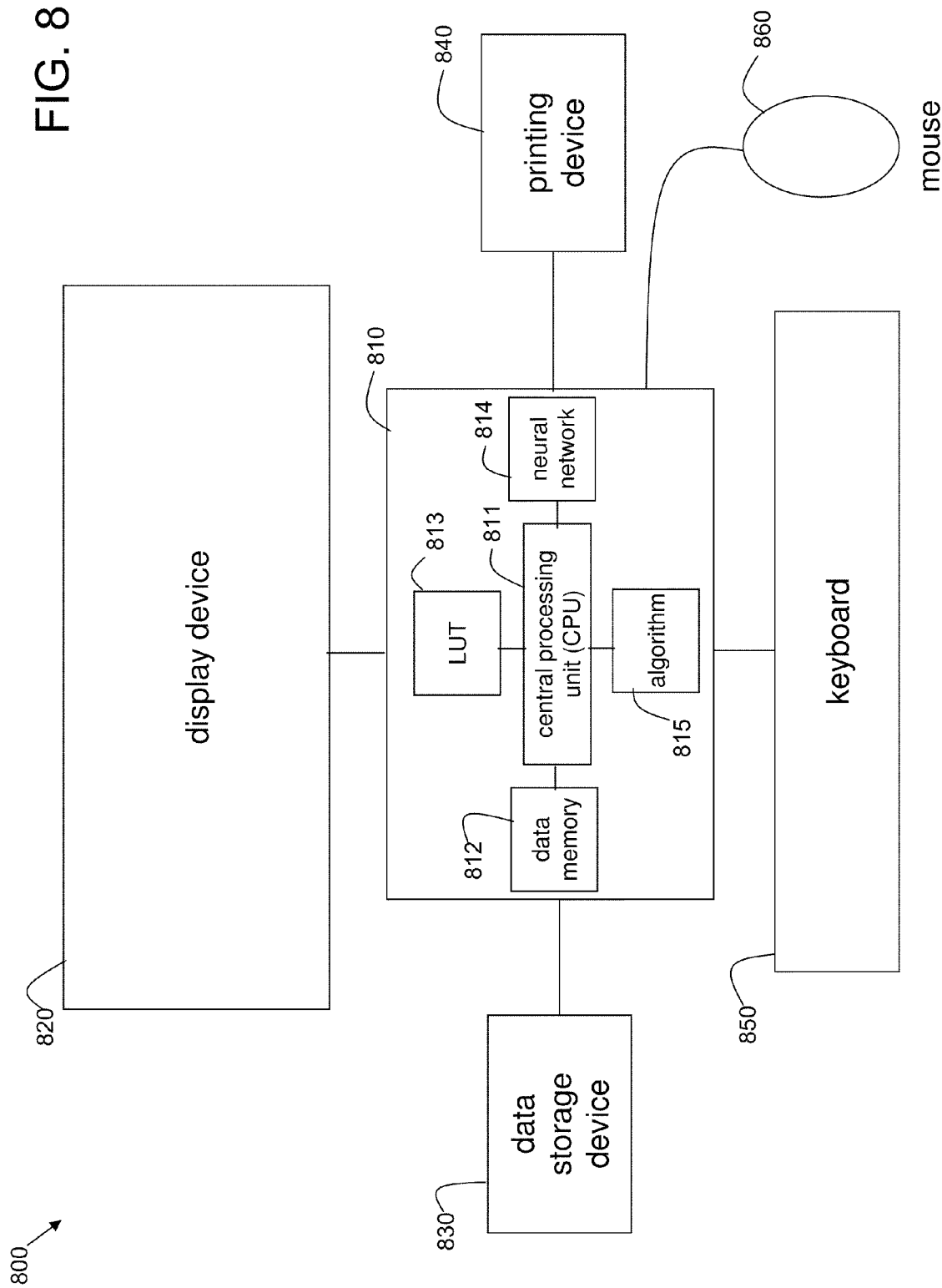

SYSTEM AND METHOD FOR DENTITION SPECIFIC IMAGE ENHANCEMENT

TECHNICAL FIELD

Certain embodiments relate to image enhancement. More particularly, certain embodiments relate to systems, methods, and non-transitory computer-readable media to automatically tailor image parameter settings based on at least a dentition characteristic of a dental patient.

BACKGROUND

A dentist tends to encounter dental patients having many different types of dentition characteristics. These various dentition characteristics may include, for example, a capped tooth, a tooth having a filling, bridge work, an implant, a root canal, and a cracked or broken tooth. Furthermore, these various dentition characteristics can have an affect on the quality of X-ray images of a patient's teeth as acquired by a dentist or a dental technician. For example, a particular set of X-ray machine settings may result in a good image for one type of dentition but not for another.

Further limitations and disadvantages of conventional, traditional, and proposed approaches will become apparent to one of skill in the art, through comparison of such systems and methods with the subject matter of the present application as set forth in the remainder of the present application with reference to the drawings.

SUMMARY

An embodiment of the present invention comprises a method to automatically tailor image parameter settings in a dental X-ray imaging system having a user interface and an image processing subsystem. The method includes selecting at least one dentition characteristic corresponding to a dentition of a patient to be imaged via the user interface of the dental X-ray imaging system. The method further includes selecting at least one non-dentition characteristic corresponding to the patient to be imaged via the user interface of the dental X-ray imaging system. The method also includes automatically determining at least one X-ray exposure setting in response to the at least one dentition characteristic and the at least one non-dentition characteristic via the image processing subsystem of the X-ray imaging system. The method further includes automatically generating a set of image parameter settings capable of being applied to acquired X-ray image data, being representative of the dentition of the patient, in response to the at least one dentition characteristic, the at least one non-dentition characteristic, and the at least one X-ray exposure setting via the image processing subsystem of the X-ray imaging system. The method may also include acquiring at least one set of X-ray image data of the dentition of the patient using the X-ray imaging system set to the at least one X-ray exposure setting. The method may further include automatically applying the set of image parameter settings to the at least one set of acquired X-ray image data via the image processing subsystem to generate at least one set of display image data. The method may also include displaying the at least one set of display image data. The at least one dentition characteristic includes at least one of a tooth identifier, a capped tooth flag, a tooth filling flag, a teeth bridge work flag, a tooth implant flag, a root canal flag, a cracked or broken tooth flag, a strong/weak enamel flag, a braces flag, and an image type. The at least one non-dentition characteristic includes at least one of a gender of the patient, a race or ethnicity of the patient, a weight of the patient, a height of the patient, an age of the patient, a pregnancy status of the patient, and a species of the patient. In accordance with an embodiment of the present invention, the image processing subsystem employs at least one predefined look-up table to accomplish the method step of automatically generating a set of image parameter settings. In accordance with another embodiment of the present invention, the image processing subsystem employs at least one programmed algorithm to accomplish the method step of automatically generating a set of image parameter settings. In accordance with a further embodiment of the present invention, the image processing subsystem employs at least one neural network configuration to accomplish the method step of automatically generating a set of image parameter settings. In accordance with yet another embodiment of the present invention, the image processing subsystem employs at least one evolutionary algorithm to accomplish the method step of automatically generating a set of image parameter settings. The set of image parameter settings may include at least one of a brightness setting, a contrast setting, a gamma setting, a filter setting, a threshold setting, and a color map. The at least one X-ray exposure setting may include at least one of an exposure time setting, a current setting, a kilovolt peak (KVP) setting, and a milliamp seconds (mAs) setting.

Another embodiment of the present invention comprises a dental X-ray imaging system to automatically tailor image parameter settings. The dental X-ray imaging system includes means for selecting at least one dentition characteristic corresponding to a dentition of a patient to be imaged. The dental X-ray imaging system further includes means for selecting at least one non-dentition characteristic corresponding to the patient to be imaged. The dental X-ray imaging system also includes means for automatically determining at least one X-ray exposure setting in response to the at least one dentition characteristic and the at least one non-dentition characteristic. The dental X-ray imaging system further includes means for automatically generating a set of image parameter settings capable of being applied to acquired X-ray image data, being representative of the dentition of the patient, in response to the at least one dentition characteristic, the at least one non-dentition characteristic, and the at least one X-ray exposure setting. The system may further include means for acquiring at least one set of X-ray image data of the dentition of the patient using the at least one X-ray exposure setting. The system may also include means for automatically applying the set of image parameter settings to the at least one set of acquired X-ray image data to generate at least one set of display image data. The system may further include means for displaying the at least one set of display image data. The at least one dentition characteristic includes at least one of a tooth identifier, a capped tooth flag, a tooth filling flag, a teeth bridge work flag, a tooth implant flag, a root canal flag, a cracked or broken tooth flag, a strong/weak enamel flag, a braces flag, and an image type. The at least one non-dentition characteristic includes at least one of a gender of the patient, a race or ethnicity of the patient, a weight of the patient, a height of the patient, an age of the patient, a pregnancy status of the patient, and a species of the patient. In accordance with an embodiment of the present invention, the means for automatically generating a set of image parameter settings includes means for addressing at least one predefined look-up table. In accordance with another embodiment of the present invention, the means for automatically generating a set of image parameter settings includes means for implementing at least one programmed algorithm. In accordance with a further embodiment of the present invention, the means for automatically generating a set of image parameter settings includes means for implementing at least one neural network configuration. In accordance with still another embodiment of the present invention, the means for automatically generating a set of image parameter settings includes means for implementing at least one evolutionary algorithm. The set of image parameter settings may include at least one of a brightness setting, a contrast setting, a gamma setting, a filter setting, a threshold setting, and a color map. The at least one X-ray exposure setting may include at least one of an exposure time setting, a current setting, a kilovolt peak (KVP) setting, and a milliamp seconds (mAs) setting.

A further embodiment of the present invention comprises a computer system to automatically tailor image parameter settings. The computer system includes a processing architecture of hardware and software configured and programmed to: facilitate user selection of at least one dentition characteristic corresponding to a dentition of a patient to be imaged by a dental X-ray imaging system; facilitate user selection of at least one non-dentition characteristic corresponding to the patient to be imaged by a dental X-ray imaging system; automatically determine at least one X-ray exposure setting in response to the at least one dentition characteristic and the at least one non-dentition characteristic; and automatically generate a set of image parameter settings capable of being applied to acquired X-ray image data, being representative of the dentition of the patient, in response to the at least one dentition characteristic, the at least one non-dentition characteristic, and the at least one X-ray exposure setting. The computer system further includes a data memory device operatively connected to the processing architecture and configured to store the set of image parameter settings. The computer system also includes an output device operatively connected to the data memory device and configured to output the set of image parameter settings for use by a user. The output device may include at least one of a display device, a data storage device, and a printing device. The at least one dentition characteristic includes at least one of a tooth identifier, a capped tooth flag, a tooth filling flag, a teeth bridge work flag, a tooth implant flag, a root canal flag, a cracked or broken tooth flag, a strong/weak enamel flag, a braces flag, and an image type. The at least one non-dentition characteristic includes at least one of a gender of the patient, a race or ethnicity of the patient, a weight of the patient, a height of the patient, an age of the patient, a pregnancy status of the patient, and a species of the patient. In accordance with an embodiment of the present invention, the processing architecture employs at least one predefined look-up table to automatically generate the set of image parameter settings. In accordance with another embodiment of the present invention, the processing architecture employs at least one programmed algorithm to automatically generate the set of image parameter settings. In accordance with a further embodiment of the present invention, the processing architecture employs at least one neural network configuration to automatically generate the set of image parameter settings. In accordance with still another embodiment of the present invention, the processing architecture employs at least one evolutionary algorithm to automatically generate the set of image parameter settings. The set of image parameter settings may include at least one of a brightness setting, a contrast setting, a gamma setting, a filter setting, a threshold setting, and a color map. The at least one X-ray exposure setting may include at least one of an exposure time setting, a current setting, a kilovolt peak (KVP) setting, and a milliamp seconds (mAs) setting.

Another embodiment of the present invention comprises a non-transitory computer-readable media having computer-readable instructions recorded thereon and capable of being executed by a computer system for automatically tailoring image parameter settings. The instructions include instructions for facilitating user selection of at least one dentition characteristic corresponding to a dentition of a patient to be imaged by a dental X-ray imaging system. The instructions further include instructions for facilitating user selection of at least one non-dentition characteristic corresponding to the patient to be imaged by a dental X-ray imaging system. The instructions also include instructions for automatically determining at least one X-ray exposure setting in response to the at least one dentition characteristic and the at least one non-dentition characteristic. The instructions further include instructions for automatically generating a set of image parameter settings capable of being applied to acquired X-ray image data, being representative of the dentition of the patient, in response to the at least one dentition characteristic, the at least one non-dentition characteristic, and the at least one X-ray exposure setting. The at least one dentition characteristic includes at least one of a tooth identifier, a capped tooth flag, a tooth filling flag, a teeth bridge work flag, a tooth implant flag, a root canal flag, a cracked or broken tooth flag, a strong/weak enamel flag, a braces flag, and an image type. The at least one non-dentition characteristic includes at least one of a gender of the patient, a race or ethnicity of the patient, a weight of the patient, a height of the patient, an age of the patient, a pregnancy status of the patient, and a species of the patient. In accordance with an embodiment of the present invention, the instructions for automatically generating a set of image parameter settings includes instructions for employing at least one predefined look-up table. In accordance with another embodiment of the present invention, the instructions for automatically generating a set of image parameter settings includes instructions for implementing at least one mathematical algorithm. In accordance with a further embodiment of the present invention, the instructions for automatically generating a set of image parameter settings includes instructions for employing at least one neural network configuration. In accordance with still another embodiment of the present invention, the instructions for automatically generating a set of image parameter settings includes instructions for implementing at least one evolutionary algorithm. The set of image parameter settings may include at least one of a brightness setting, a contrast setting, a gamma setting, a filter setting, a threshold setting, and a color map. The at least one X-ray exposure setting may include at least one of an exposure time setting, a current setting, a kilovolt peak (KVP) setting, and a milliamp seconds (mAs) setting.

These and other novel features of the subject matter of the present application, as well as details of illustrated embodiments thereof, will be more fully understood from the following description and drawings.

BRIEF DESCRIPTION OF THE DRAWINGS

FIG. 2 illustrates lists of example embodiments of a set of dentition characteristics, a set of non-dentition characteristics, a set of X-ray exposure settings, and a set of image parameter settings tailored by the dental X-ray imaging system of FIG. 1;

FIG. 7 illustrates a flow chart of an example embodiment of a method to automatically tailor image parameter settings in the dental X-ray imaging system of FIG. 1; and FIG. 8 illustrates a schematic block diagram of an example embodiment of a computer system to automatically tailor image parameter settings.

DETAILED DESCRIPTION

Figure 1:
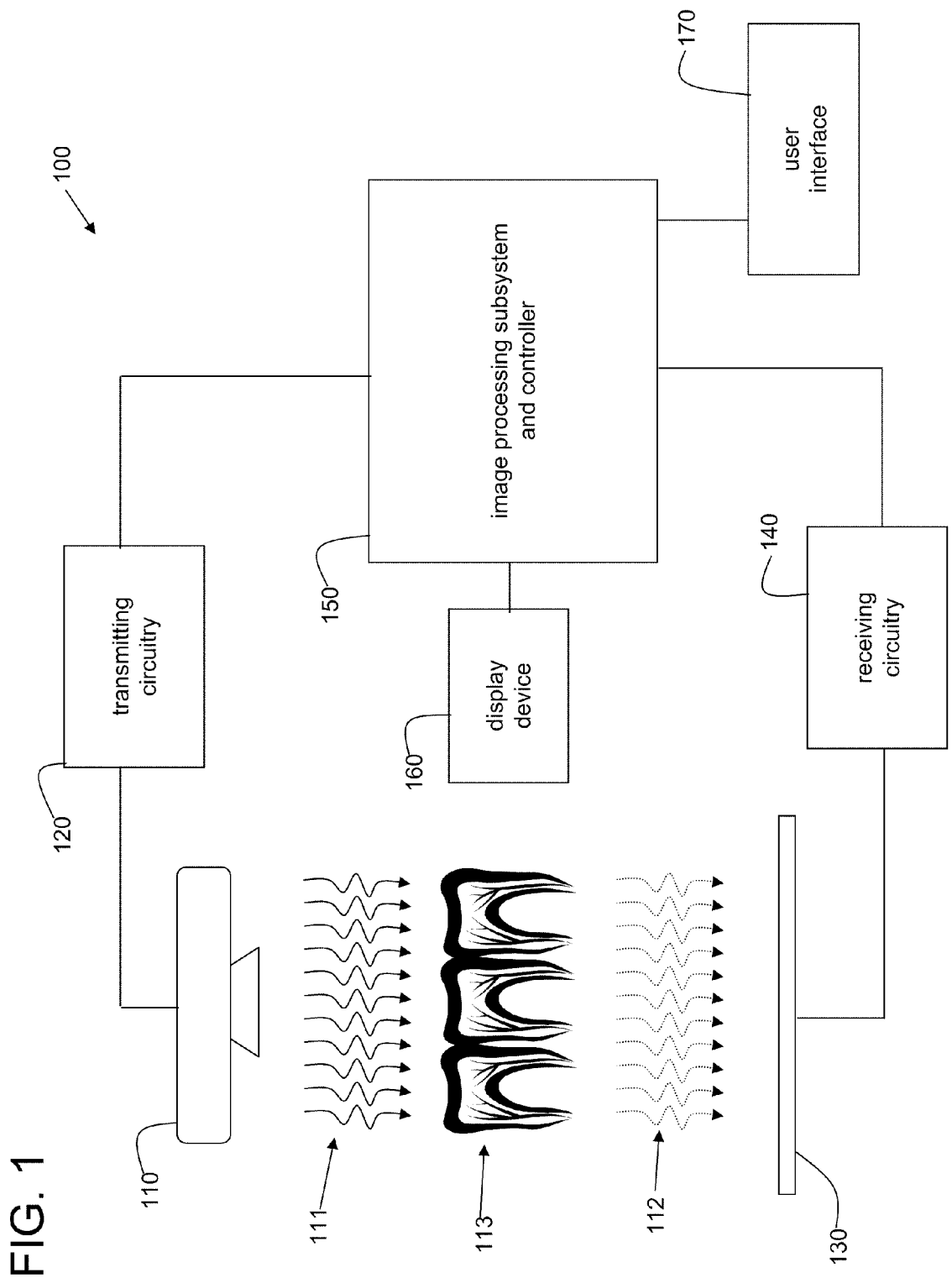
FIG. 1 illustrates a schematic diagram of an example embodiment of a dental X-ray imaging system having an image processing subsystem to automatically tailor image parameter settings.

FIG. 1 illustrates a schematic diagram of an example embodiment of a dental X-ray imaging system 100 having an image processing subsystem to automatically tailor image parameter settings. The system 100 includes an X-ray source 110 (e.g., an X-ray tube), transmitting circuitry 120 operationally connected to the X-ray source 110, an X-ray detector or sensor 130, and receiving circuitry 140 operationally connected to the X-ray detector 130. Such X-ray sources, transmitting circuitry, X-ray detectors, and receiving circuitry are well known in the art.

The dental X-ray imaging system 100 further includes an image processing subsystem and controller 150 operationally interfacing to the transmitting circuitry 120 and the receiving circuitry 140. The image processing subsystem and controller 150 is programmed and configured with computer software instructions and hardware for controlling the transmitting circuitry 120 and the receiving circuitry 130 during image acquisition, and for performing image processing and image parameter tailoring functions as described herein. In FIG. 1, the image processing subsystem and controller 150 is shown as one element. However, the image processing subsystem and controller 150 could be broken up into two elements, an image processing subsystem and a controller.

The image processing subsystem portion of the image processing subsystem and controller 150 may be configured using at least one of programmed algorithms, neural networks, and look-up tables (LUTs) to automatically tailor image parameter settings, in accordance with various embodiments of the present invention. The system 100 also includes a display device 160 and a user interface 170 operationally interfacing to the image processing subsystem and controller 150. The user interface may be a keyboard device, a mouse device, a touchscreen display, or any of a number of various types of possible user interfaces.

During operation, the X-ray source 110 of the system 100 emits X-rays that pass through the dentition 113 of a patient and are received by the X-ray detector 130. The structure of the dentition 113 alters the intensity of the X-rays as the X-rays pass through the dentition 113, allowing image data to be captured by the X-ray detector 130 and receiving circuitry 140 and passed on to the image processing subsystem and controller 150. Different patients can have many different types of dentition characteristics. These various dentition characteristics may include, for example, a capped tooth, a tooth having a filling, bridge work, an implant, a root canal, and a cracked or broken tooth. Furthermore, these various dentition characteristics can have an affect on the quality of X-ray images of a patient's teeth as acquired by the system 100.

In accordance with an embodiment of the present invention, the image parameter settings may be tailored within the X-ray imaging system 100 of FIG. 1 based on selected dentition characteristics, non-dentition characteristics, and X-ray exposure settings to provide an image of high image quality. FIG. 2 illustrates lists of example embodiments of a set of dentition characteristics, a set of non-dentition characteristics, a set of X-ray exposure settings, and a set of image parameter settings tailored by the dental X-ray imaging system 100 of FIG. 1. When preparing to image a patient, the dentist or dental technician uses the user interface 170 of the system 100 to select the dentition characteristics and the non-dentition characteristics corresponding to the patient such that the selected dentition characteristics and non-dentition characteristics are provided to the image processing subsystem and controller 150.

The dentition characteristics may include a tooth identifier, a capped tooth flag or indicator, a tooth filling flag or indicator, a teeth bridge work flag or indicator, a tooth implant flag or indicator, a root canal flag or indicator, a cracked or broken tooth flag or indicator, a strong/weak enamel flag or indicator, a braces flag or indicator, and an image type. In accordance with an embodiment of the present invention, the tooth identifier is a tooth number (e.g., a number from 1 to 32 from the standard tooth numbering chart, see FIG. 3) which identifies each tooth to be imaged. The capped tooth flag or indicator is a binary number (e.g., 0 or 1) indicating if any of the teeth to be imaged are capped. Similarly, the teeth bridge work flag or indicator is a binary number indicating if any bridge work is present among the teeth to be imaged, the tooth implant flag or indicator is a binary number indicating if a tooth to be imaged is an implant, the root canal flag or indicator is a binary number indicating if a tooth to be imaged has had a root canal procedure performed, and the cracked or broken tooth flag or indicator is a binary number indicating if a tooth to be imaged is cracked or broken. The strong/weak enamel flag is a binary number where, for example, '0' indicates a strong enamel condition and '1' indicates a weak enamel condition of the dentition to be imaged. The braces flag is a binary number indicating if orthodontic braces are present on the dentition to be imaged. Image type specifies the type of image to be acquired such as, for example, a bitewing image or a pan-oral image. Other dentition characteristics are possible as well, in accordance with various embodiments of the present invention.

The non-dentition characteristics may include a gender of the patient (i.e., male or female), a race or ethnicity of the patient (e.g., black, Asian, white), a weight of the patient (e.g. in pounds), a height of the patient (e.g., in inches), and age of the patient (e.g., in years), a pregnancy status of the patient (e.g., pregnant or not pregnant), and a species of the patient (e.g., human, dog, cat, horse, etc.). Other non-dentition characteristics are possible as well, in accordance with various embodiments of the present invention.

The X-ray exposure settings may include an exposure time setting (e.g., in milliseconds), a current setting (e.g., in milliamps), a kilovolt peak (KVP) setting, and a milliamp seconds (mAs) setting. The mAs setting is a combination of the exposure time setting and the current setting. The mAs setting affects the quantity of X-ray photons produced and the amount of blackening or density in the resultant image. For example, 4 milliamps provided for 82 milliseconds provides 0.328 mAs of exposure. The KVP setting affects the quality of the X-ray beam produced and the contrast or gray scale in the resultant image. A higher KVP provides lower contrast in the resultant image. For example, when a KVP of "70" is selected, the maximum kilovolts that are produced by the X-ray imaging system 100 is 70 kV (i.e., 70,000 volts). X-ray data is acquired using the selected X-ray exposure settings. Other X-ray exposure settings are possible as well, in accordance with various embodiments of the present invention.

The image parameter settings may include a brightness setting, a contrast setting, a gamma setting, a filter setting, a threshold setting, and a color map (e.g. a gray-scale map). The image parameter settings are applied to acquired X-ray image data to produce an image for display having the desired image quality characteristics. Other image parameter settings are possible as well, in accordance with various embodiments of the present invention.

Brightness is a term used to describe the overall amount of light in an image. When brightness is increased, the value of every pixel in the image is increased (e.g., closer to a value of 255 or white). When brightness is decreased, the value of every pixel in the image is decreased (e.g., closer to a value of 0 or black).

Contrast is a term used to describe the degree of difference between the brightest and darkest components in an image. The amount of the intensity scale (e.g., 0 to 255) used by an image is the dynamic range of the image. An image with "good" contrast has a "good" dynamic range. During a contrast adjustment, each pixel value in an image is scaled by a contrast value which results in redistributing the intensities over a wider or narrow range. Increasing the contrast spreads the pixel values across a wider range, and decreasing the contrast squeezes the pixel values into a narrower range.

Gamma is a term used to describe a type of image correction which is a specialized form of contrast enhancement and is designed to enhance contrast in the very dark or very light regions of an image. Adjusting the gamma setting modifies an image by applying standard, nonlinear gamma curves to the intensity scale. For example, a gamma value of 1 is equivalent to the identity curve (no change in the intensity scale). An increase in the gamma value (setting to a value greater than 1) generally results in lightening an image and increasing the contrast in the darker areas of the image. A decrease in the gamma value (setting to a value less than 1) generally results in darkening of the image and emphasizes contrast in the lighter areas of the image.

The term filter is used to describe any of a plurality of different types of filtering operations than may be performed on the pixel values of an image. A filter may be one-dimensional in the vertical direction, one-dimensional in the horizontal direction, or two-dimensional in both the vertical and horizontal directions, based on a predefined kernel of pixels. A filter may provide a low-pass filtering operation, a high-pass filtering operation, a band-pass filtering operation, a median filtering operation, or any of a number of other possible filtering operations which are well known in the art.

The term threshold setting is used to describe a pixel value level for which pixel values in an image below that pixel value setting are thresholded out and not displayed (or displayed as black, for example). Alternatively, the term threshold setting is used to describe a pixel value level for which pixel values in an image above that pixel value setting are thresholded out and not displayed (or displayed as black, for example). As a further alternative, two threshold settings may be defined for which pixel values in an image being between the threshold values are displayed normally, and the rest are filtered out (or displayed as black, for example). As still a further alternative, two threshold settings may be defined for which pixel values in an image being between the threshold values are filtered out (or displayed as black, for example), and the rest are displayed normally.

The term color map is used to describe the gray-scale colors that get assigned to the image pixel values of an image, in accordance with an embodiment of the present invention. For example, in an image having pixel values spanning the dynamic range of 0 to 255, a linear gray-scale map may be applied, where a pixel value of 0 is assigned the black color, a pixel value of 255 is assigned the white color, and the pixel values from 1 to 254 are linearly distributed over the remaining gray-scale colors. Other types of gray-scale color maps may be applied as well which distribute the gray-scale colors in a non-linear (e.g., logarithmic) manner or piece-wise linear manner, for example.

Figure 4:
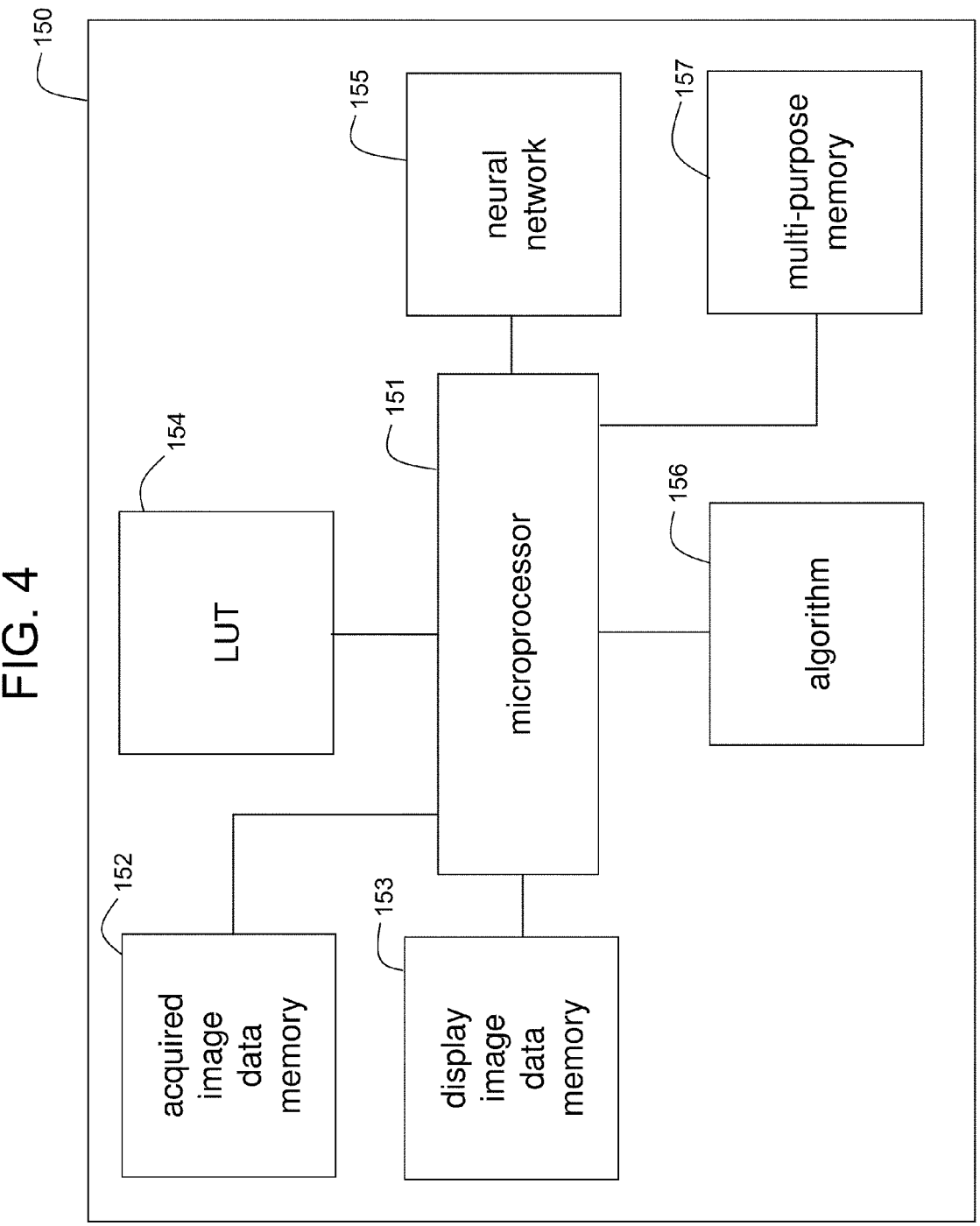
FIG. 4 illustrates a schematic bock diagram of an example embodiment of the image processing subsystem of the dental X-ray imaging system of FIG. 1.

FIG. 4 illustrates a schematic bock diagram of an example embodiment of the image processing subsystem and controller 150 of the dental X-ray imaging system 100 of FIG. 1. The subsystem and controller 150 includes a microprocessor 151, an acquired image data memory 152 operationally interfacing to the microprocessor 151, and a display image data memory or buffer 153 operationally interfacing to the microprocessor 151. The subsystem and controller 150 also includes at least one of a look-up table (LUT) 154 operationally interfacing to the microprocessor 151, a neural network configuration 155 operationally interfacing with the microprocessor 151, a programmed algorithm 156 capable of being executed on the microprocessor 151. The subsystem and controller 150 further includes a multi-purpose memory 157 operationally interfacing to the microprocessor 151 and capable of storing, for example, image parameter settings as well as other information.

Figure 5:
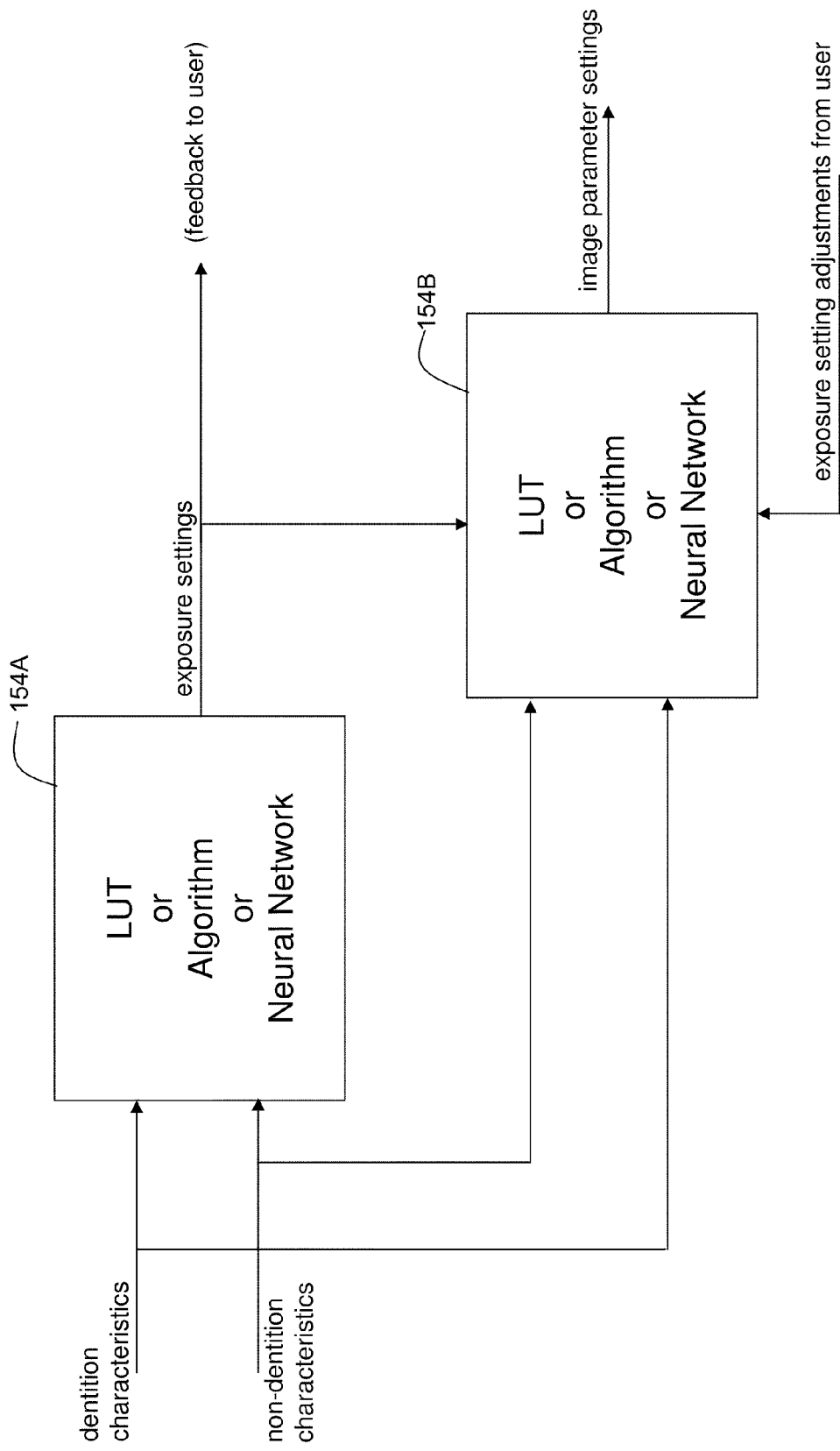
FIG. 5 illustrates a functional block diagram of a first example embodiment of a portion of the image processing subsystem of FIG. 1 and FIG. 4.

FIG. 5 illustrates a functional block diagram of a first example embodiment of a portion of the image processing subsystem and controller 150 of FIG. 1 and FIG. 4. A first LUT 154A is operationally connected to a second LUT 154B. The LUTs may be, for example, EEPROM devices having addressable inputs and adaptable outputs. The inputs to the first LUT 154A are dentition characteristics and non-dentition characteristics. The LUT 154A is programmed to output tailored or recommended exposure settings in dependence on the input dentition characteristics and non-dentition characteristics.

For example, if the dentition characteristics indicate the particular teeth to be imaged (e.g., via tooth numbers) and that one of the teeth to be imaged has had a root canal done, and the non-dentition characteristics indicate that the weight of the patient is 300 pounds, then the resultant exposure settings out of the LUT 154A may be a current setting of 4 milliamps, a kilovolt peak (KVP) setting of 70, and an exposure time setting of 82 milliseconds. If, for example, the dentition characteristics indicate the particular teeth to be imaged and that all of the teeth to be imaged have been capped, and the non-dentition characteristics indicate that the weight of the patient is 150 pounds and that the patient is pregnant, then the resultant exposure settings out of the LUT 154A may be a current setting of 4 milliamps, a kilovolt peak (KVP) setting of 70, and an exposure time setting of 42 milliseconds. The resultant exposure settings out of the LUT 154A may be provided to the display device 160 to provide feedback to a user such that the user may be able to, via the user interface 170, acknowledge acceptance of the displayed exposure settings or change the exposure settings.

Furthermore, the dentition characteristics, the non-dentition characteristics, and the exposure settings are input to the second LUT 154B. The LUT 154B is programmed to output tailored image parameter settings in dependence on the input dentition characteristics, the non-dentition characteristics, and the exposure settings. The image parameter settings may be stored in the multi-purpose memory 157 via the microprocessor 151 (see FIG. 4). Continuing with the example, the input dentition characteristics indicate the particular teeth to be imaged (e.g., via teeth number) and that one of the teeth to be imaged has had a root canal done, and the non-dentition characteristics indicate that the weight of the patient is 300 pounds, and the resultant exposure settings indicate a current setting of 4 milliamps, a kilovolt peak (KVP) setting of 70, and an exposure time setting of 82 milliseconds.

The resultant image parameter settings out of the LUT 154B may be a brightness setting of 50%, a contrast setting of 70%, a gamma setting of 1.5 (e.g., on a scale of 0 to 2), a filter setting of low-pass (e.g., from selections of low-pass, band-pass, and high-pass), a threshold setting of 5 (e.g. on a scale of 0 to 255), and a linear gray-scale color map (from selections of a linear, a logarithmic, a piecewise linear, and an S-curve gray-scale color map). If the user decides to change the exposure settings, the changed exposure settings may be input to the LUT 154B to adjust the image parameter settings.

In accordance with other embodiments of the present invention, instead of being a LUT, elements 154A and 154B may be implemented as a neural network configuration, or as an algorithm operating on the microprocessor 151. However, any combination of LUTs, algorithms, and neural networks may be used according to sound engineering judgment.

A neural network configuration is a tool that is able to capture and represent complex relationships between input data and output data. A neural network configuration effectively acquires knowledge through learning or training. This trained knowledge is stored within inter-neuron connections weightings called synaptic weights. A neural network configuration is capable of representing both linear and non-linear relationships between input data and output data, and learn these relationships from the data being modeled. A common type of neural network configuration is a multilayer perceptron (MLP) which requires a desired output in order to learn or train up. This type of neural network configuration creates a model that correctly maps input data to output data using training data such that the neural network configuration may be used to produce adequate output data when presented with real-world, non-training input data. A neural network configuration may be implemented in hardware such as, for example, using a digital signal processor (DSP), or may be implemented as a set of software instructions operating on the microprocessor 151, in accordance with various embodiments of the present invention.

An algorithm may be a mathematical algorithm operating on input data to produce output data and may be implemented on the microprocessor 151 as a set of software instructions, or may be configured in hardware, for example, as a DSP. An algorithm may be derived from a genetic or evolutionary algorithm. An evolutionary algorithm uses concepts of natural selection and survival of the fittest to evolve, for example, a mathematical algorithm over many iterations or generations. An evolutionary algorithm performs a search from a population of solutions. Each iteration or generation of the evolutionary algorithm includes competitive selections and gets rid of lesser solutions.

Solutions with high scores or high fitness are combined with other solutions through genetic operations such as crossover, and are also allowed to mutate by making relatively small changes to a portion of a solution. As generations progress, a set of best solutions represented as mathematical or logical algorithms are derived. An evolutionary algorithm may be implemented off-line from the dental X-ray imaging system 100 and the resultant best solution may be implemented as a software algorithm on the microprocessor 151.

Alternatively, an evolutionary algorithm may be implemented on the dental X-ray imaging system 100 and, every time a patient is imaged, the user may adjust certain X-ray exposure settings and image parameter settings to create a desired image, thus allowing the evolutionary algorithm to continue to train up on real world data. Eventually, the evolutionary algorithm is trained up to such an adequate capability that the user may no longer have to make any adjustments to the settings (i.e., the algorithm immediately generates the desired settings automatically).

Figure 6:
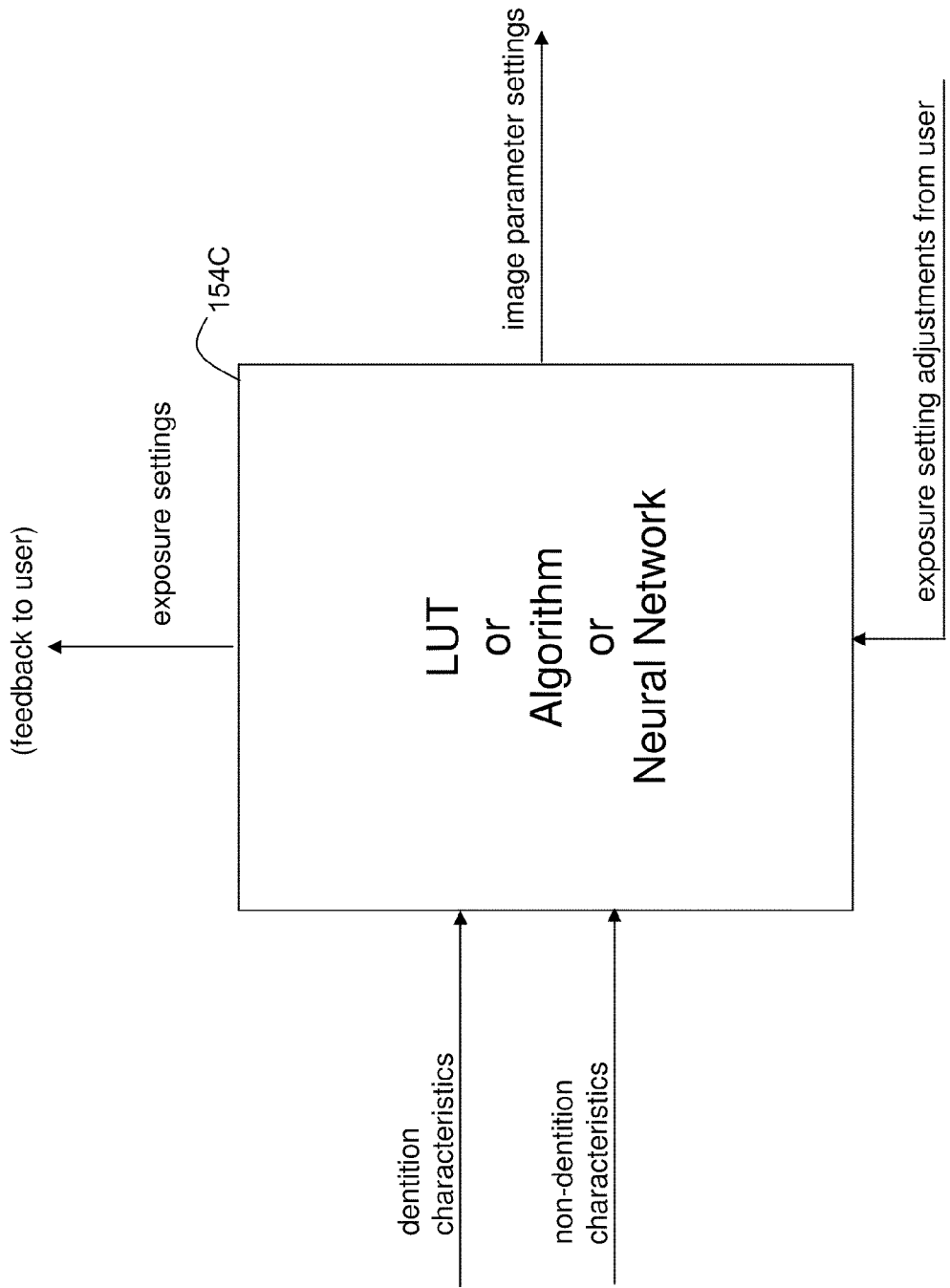
FIG. 6 illustrates a functional block diagram of a second example embodiment of a portion of the image processing subsystem of FIG. 1 and FIG. 4.

FIG. 6 illustrates a functional block diagram of a second example embodiment of a portion of the image processing subsystem 150 of FIG. 1 and FIG. 4. In this embodiment, a single LUT, algorithm, or neural network 154C is implemented. Dentition characteristics and non-dentition characteristics serve as inputs, and exposure settings and image parameter settings are resultant outputs. However, internally to the LUT, algorithm, or neural network, the resultant exposure settings are determined and used, along with the dentition characteristics and the non-dentition characteristics, to determine the image parameter settings. The image parameter settings may be stored in the multi-purpose memory 157 via the microprocessor 151 (see FIG. 4).

Again, the output resultant exposure settings may be provided to the display device 160 to provide feedback to a user such that the user may be able to, via the user interface 170, acknowledge acceptance of the displayed exposure settings or change the exposure settings. If the user decides to change the exposure settings, the changed exposure settings may be input to the LUT, algorithm, or neural network 154C to adjust the image parameter settings.

FIG. 7 illustrates a flow chart of an example embodiment of a method 700 to automatically tailor image parameter settings in the dental X-ray imaging system 100 of FIG. 1. In step 710 of the method 700, select at least one dentition characteristic corresponding to a dentition of a patient to be imaged. In step 720 of the method 700, select at least one non-dentition characteristic corresponding to the patient to be imaged. In step 730 of the method 700, automatically determine at least one X-ray exposure setting in response to the at least one dentition characteristic and the at least one non-dentition characteristic. In step 740 of the method 700, automatically generate a set of image parameter settings capable of being applied to acquired X-ray image data in response to the at least one dentition characteristic, the at least one non-dentition characteristic, and the at least one X-ray exposure setting.

Figure 3:
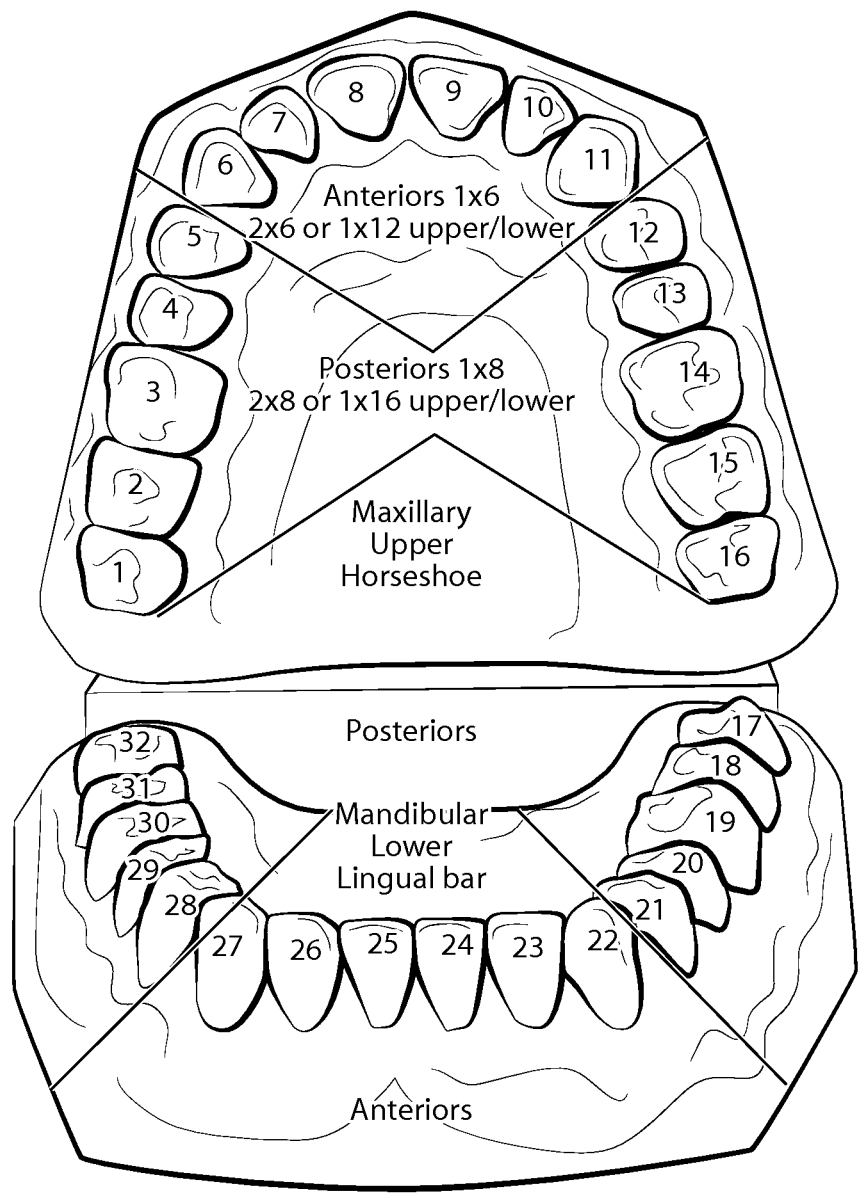
FIG. 3 illustrates a standard tooth numbering chart.

The method 700 may further include the step 750 of acquiring at least one set of X-ray image data of the dentition of the patient at the X-ray exposure setting. Referring to FIG. 3 and FIG. 4, an acquired set of X-ray image data may be sent from the receiving circuitry 140 to the acquired image data memory 152 of the image processing subsystem and controller 150 where it is stored. The method 700 may also include the step 760 of automatically applying the set of image parameter settings to the set of acquired X-ray image data to generate display image data. Referring to FIG. 4, the microprocessor 152 may read in the acquired set of X-ray image data from the acquired image data memory 152 and further read in the image parameter settings stored in the multi-purpose memory 157 and perform processing to apply the image parameter settings to the acquired image data memory. The resultant display image data may be stored in the display image data memory 153. The method 700 may further include the step 770 of displaying the display image data on the display device 160 by reading out the display image data memory 153 to the display device 160.

FIG. 8 illustrates a schematic block diagram of an example embodiment of a computer system 800 to automatically tailor image parameter settings. The computer system 800 differs from the dental X-ray imaging system 100 of FIG. 1 in that the computer system 800 is not used to acquire and process X-ray imaging data but, instead, is used to generate X-ray exposure settings and image parameter settings offline from a dental X-ray imaging system. The settings may then be transferred (e.g., in the form of a file) to a dental X-ray imaging system for use thereon to apply the image parameter settings and the X-ray exposure settings to acquired X-ray data for a patient.

The computer system 800 includes a processing subsystem 810, a display device 820 operatively connected to the processing subsystem 810, a data storage device 830 operatively connected to the processing subsystem 810, a printing device 840 operatively connected to the processing subsystem 810, a keyboard device 850 operatively connected to the processing subsystem 810, and a mouse device 860 operatively connected to the processing subsystem 810.

The processing subsystem 810 includes a central processing unit (CPU) 811 and a data memory 812 operatively connected to the CPU 811. The data memory 812 may be used for any of a plurality of purposes including but not limited to storing image parameter settings and exposure settings. The processing subsystem 810 also includes at least one of a look-up table (LUT) 813 operatively connected to the CPU 811, a neural network configuration 814 operatively connected to the CPU 811, and a programmed algorithm 815 capable of being executed on the CPU 811.

The processing subsystem 810 operates in a similar manner to the image processing subsystem 150 of FIG. 1 in that dentition characteristics and non-dentition characteristics input by a user (e.g., via the keyboard 850 and mouse 860) are used to generate exposure settings. The dentition characteristics, the non-dentition characteristics, and the exposure settings are then used to generate the image parameter settings, using a LUT, an algorithm, a neural network, or some combination thereof. The resultant image parameter settings and the exposure settings may be stored on the data storage device 830 for later use on an X-ray imaging system. Furthermore, resultant image parameter settings and exposure settings may be displayed on the display device 820 and printed using the printing device 840.

In accordance with an embodiment of the present invention, a LUT, an algorithm, or a neural network configuration for generating image parameter settings may be stored as recorded computer-readable instructions on a non-transitory computer-readable media such as, for example, a CD, a hard drive, or a flash drive. The instructions may be capable of being executed by the computer system 800.

In summary, systems, methods, and computer readable media to automatically tailor image parameter settings used in a dental X-ray imaging system are disclosed. At least one dentition characteristic and at least one non-dentition characteristic are selected and used to automatically determine at least one X-ray exposure setting for a patient to be imaged. The at least one dentition characteristic, the at least one non-dentition characteristic, and the at least one X-ray exposure setting are used to automatically generate a set of image parameter settings capable of being applied to acquired X-ray image data, being representative of the dentition of the patient.

While the claimed subject matter of the present application has been described with reference to certain embodiments, it will be understood by those skilled in the art that various changes may be made and equivalents may be substituted without departing from the scope of the claimed subject matter. In addition, many modifications may be made to adapt a particular situation or material to the teachings of the claimed subject matter without departing from its scope. Therefore, it is intended that the claimed subject matter not be limited to the particular embodiment disclosed, but that the claimed subject matter will include all embodiments falling within the scope of the appended claims.

What is claimed is:

1. A method to automatically tailor image parameter settings in a dental X-ray imaging system having a user interface and an image processing subsystem, said method comprising:
   selecting at least one dentition characteristic corresponding to a dentition of a patient to be imaged via said user interface of said dental X-ray imaging system;
   selecting at least one non-dentition characteristic corresponding to said patient to be imaged via said user interface of said dental X-ray imaging system;
   automatically determining at least one X-ray exposure setting in response to said at least one dentition characteristic and said at least one non-dentition characteristic via said image processing subsystem of said X-ray imaging system; and
   automatically generating a set of image parameter settings capable of being applied to acquired X-ray image data, being representative of said dentition of said patient, in response to said at least one dentition characteristic, said at least one non-dentition characteristic, and said at least one X-ray exposure setting via said image processing subsystem of said X-ray imaging system.

2. The method of claim 1 further comprising acquiring at least one set of X-ray image data of said dentition of said patient using said X-ray imaging system set to said at least one X-ray exposure setting.

3. The method of claim 2 further comprising automatically applying said set of image parameter settings to said at least one set of acquired X-ray image data via said image processing subsystem to generate at least one set of display image data.

4. The method of claim 3 further comprising displaying said at least one set of display image data.

5. The method of claim 1 wherein said at least one dentition characteristic includes at least one of a tooth identifier, a capped tooth flag, a tooth filling flag, a teeth bridge work flag, a tooth implant flag, a root canal flag, a cracked or broken tooth flag, a strong/weak enamel flag, a braces flag, and an image type.

6. The method of claim 1 wherein said at least one non-dentition characteristic includes at least one of a gender of said patient, a race or ethnicity of said patient, a weight of said patient, a height of said patient, an age of said patient, a pregnancy status of said patient, and a species of said patient.

7. The method of claim 1 wherein said image processing subsystem employs at least one predefined look-up table to accomplish said method step of automatically generating a set of image parameter settings.

8. The method of claim 1 wherein said image processing subsystem employs at least one programmed algorithm to accomplish said method step of automatically generating a set of image parameter settings.

9. The method of claim 1 wherein said image processing subsystem employs at least one neural network configuration to accomplish said method step of automatically generating a set of image parameter settings.

10. The method of claim 1 wherein said image processing subsystem employs at least one evolutionary algorithm to accomplish said method step of automatically generating a set of image parameter settings.

11. The method of claim 1 wherein said set of image parameter settings includes at least one of a brightness setting, a contrast setting, a gamma setting, a filter setting, a threshold setting, and a color map.

12. The method of claim 1 wherein said at least one X-ray exposure setting includes at least one of an exposure time setting, a current setting, a kilovolt peak (KVP) setting, and a milliamp seconds (mAs) setting.

13. A dental X-ray imaging system to automatically tailor image parameter settings, said system comprising:
    means for selecting at least one dentition characteristic corresponding to a dentition of a patient to be imaged;
    means for selecting at least one non-dentition characteristic corresponding to said patient to be imaged;
    means for automatically determining at least one X-ray exposure setting in response to said at least one dentition characteristic and said at least one non-dentition characteristic; and
    means for automatically generating a set of image parameter settings capable of being applied to acquired X-ray image data, being representative of said dentition of said patient, in response to said at least one dentition characteristic, said at least one non-dentition characteristic, and said at least one X-ray exposure setting.

14. The system of claim 13 further comprising means for acquiring at least one set of X-ray image data of said dentition of said patient using said at least one X-ray exposure setting.

15. The system of claim 14 further comprising means for automatically applying said set of image parameter settings to said at least one set of acquired X-ray image data to generate at least one set of display image data.

16. The system of claim 15 further comprising means for displaying said at least one set of display image data.

17. The system of claim 13 wherein said at least one dentition characteristic includes at least one of a tooth identifier, a capped tooth flag, a tooth filling flag, a teeth bridge work flag, a tooth implant flag, a root canal flag, a cracked or broken tooth flag, a strong/weak enamel flag, a braces flag, and an image type.

18. The system of claim 13 wherein said at least one non-dentition characteristic includes at least one of a gender of said patient, a race or ethnicity of said patient, a weight of said patient, a height of said patient, an age of said patient, a pregnancy status of said patient, and a species of said patient.

19. The system of claim 13 wherein said means for automatically generating a set of image parameter settings includes means for addressing at least one predefined look-up table.

20. The system of claim 13 wherein said means for automatically generating a set of image parameter settings includes means for implementing at least one programmed algorithm.

21. The system of claim 13 wherein said means for automatically generating a set of image parameter settings includes means for implementing at least one neural network configuration.

22. The system of claim 13 wherein said means for automatically generating a set of image parameter settings includes means for implementing at least one evolutionary algorithm.

23. The system of claim 13 wherein said set of image parameter settings includes at least one of a brightness setting, a contrast setting, a gamma setting, a filter setting, a threshold setting, and a color map.

24. The system of claim 13 wherein said at least one X-ray exposure setting includes at least one of an exposure time setting, a current setting, a kilovolt peak (KVP) setting, and a milliamp seconds (mAs) setting.

25. A computer system to automatically tailor image parameter settings, said computer system comprising:
    a processing architecture of hardware and software configured and programmed to:
        facilitate user selection of at least one dentition characteristic corresponding to a dentition of a patient to be imaged by a dental X-ray imaging system,
        facilitate user selection of at least one non-dentition characteristic corresponding to said patient to be imaged by a dental X-ray imaging system,
        automatically determine at least one X-ray exposure setting in response to said at least one dentition characteristic and said at least one non-dentition characteristic,
        automatically generate a set of image parameter settings capable of being applied to acquired X-ray image data, being representative of said dentition of said patient, in response to said at least one dentition characteristic, said at least one non-dentition characteristic, and said at least one X-ray exposure setting;
    a data memory device operatively connected to said processing architecture and configured to store said set of image parameter settings; and
    an output device operatively connected to said data memory device and configured to output said set of image parameter settings for use by a user.

26. The computer system of claim 25 wherein said output device includes at least one of a display device, a data storage device, and a printing device.

27. The computer system of claim 25 wherein said at least one dentition characteristic includes at least one of a tooth identifier, a capped tooth flag, a tooth filling flag, a teeth bridge work flag, a tooth implant flag, a root canal flag, a cracked or broken tooth flag, a strong/weak enamel flag, a braces flag, and an image type.

28. The computer system of claim 25 wherein said at least one non-dentition characteristic includes at least one of a gender of said patient, a race or ethnicity of said patient, a weight of said patient, a height of said patient, an age of said patient, a pregnancy status of said patient, and a species of said patient.

29. The computer system of claim 25 wherein said processing architecture employs at least one predefined look-up table to automatically generate said set of image parameter settings.

30. The computer system of claim 25 wherein said processing architecture employs at least one programmed algorithm to automatically generate said set of image parameter settings.

31. The computer system of claim 25 wherein said processing architecture employs at least one neural network configuration to automatically generate said set of image parameter settings.

32. The computer system of claim 25 wherein said processing architecture employs at least one evolutionary algorithm to automatically generate said set of image parameter settings.

33. The computer system of claim 25 wherein said set of image parameter settings includes at least one of a brightness setting, a contrast setting, a gamma setting, a filter setting, a threshold setting, and a color map.

34. The computer system of claim 25 wherein said at least one X-ray exposure setting includes at least one of an exposure time setting, a current setting, a kilovolt peak (KVP) setting, and a milliamp seconds (mAs) setting.

35. A non-transitory computer-readable media having computer-readable instructions recorded thereon and capable of being executed by a computer system for automatically tailoring image parameter settings, said instructions comprising:
instructions for facilitating user selection of at least one dentition characteristic corresponding to a dentition of a patient to be imaged by a dental X-ray imaging system;
instructions for facilitating user selection of at least one non-dentition characteristic corresponding to said patient to be imaged by a dental X-ray imaging system;
instructions for automatically determining at least one X-ray exposure setting in response to said at least one dentition characteristic and said at least one non-dentition characteristic; and
instructions for automatically generating a set of image parameter settings capable of being applied to acquired X-ray image data, being representative of said dentition of said patient, in response to said at least one dentition characteristic, said at least one non-dentition characteristic, and said at least one X-ray exposure setting.

36. The non-transitory computer-readable media of claim 35 wherein said at least one dentition characteristic includes at least one of a tooth identifier, a capped tooth flag, a tooth filling flag, a teeth bridge work flag, a tooth implant flag, a root canal flag, a cracked or broken tooth flag, a strong/weak enamel flag, a braces flag, and an image type.

37. The non-transitory computer-readable media of claim 35 wherein said at least one non-dentition characteristic includes at least one of a gender of said patient, a race or ethnicity of said patient, a weight of said patient, a height of said patient, an age of said patient, a pregnancy status of said patient, and a species of said patient.

38. The non-transitory computer-readable media of claim 35 wherein said instructions for automatically generating a set of image parameter settings include instructions for employing at least one predefined look-up table.

39. The non-transitory computer-readable media of claim 35 wherein said instructions for automatically generating a set of image parameter settings include instructions for implementing at least one mathematical algorithm.

40. The non-transitory computer-readable media of claim 35 wherein said instructions for automatically generating a set of image parameter settings include instructions for employing at least one neural network configuration.

41. The non-transitory computer-readable media of claim 35 wherein said instructions for automatically generating a set of image parameter settings include instructions for implementing at least one evolutionary algorithm.

42. The non-transitory computer-readable media of claim 35 wherein said set of image parameter settings includes at least one of a brightness setting, a contrast setting, a gamma setting, a filter setting, a threshold setting, and a color map.

43. The non-transitory computer-readable media of claim 35 wherein said at least one X-ray exposure setting includes at least one of an exposure time setting, a current setting, a kilovolt peak (KVP) setting, and a milliamp seconds (mAs) setting.

* * * * *